United States Patent [19]

Chmiel et al.

[11] Patent Number: 5,989,599
[45] Date of Patent: Nov. 23, 1999

[54] PROCESS FOR THE INTERESTERIFICATION OF PHOSPHOLIPIDS

[75] Inventors: Oliver Chmiel, Marysville, Ohio; Nicholas Melachouris, Monnaz; Helmut Traitler, Corseaux, both of Switzerland

[73] Assignee: Nestec S.A., Vevey, Switzerland

[21] Appl. No.: 08/427,544

[22] Filed: Apr. 24, 1995

[51] Int. Cl.$^6$ ...................................................... A23D 3/00
[52] U.S. Cl. ........................ 426/33; 426/601; 426/602; 426/662
[58] Field of Search ................................ 426/33, 601, 662, 426/602; 435/134

[56] References Cited

U.S. PATENT DOCUMENTS 5,314,706  5/1994  Colarow et al. ........................ 426/605

FOREIGN PATENT DOCUMENTS 63-302929  12/1988  Japan .
3109935   5/1991   Japan .
WO 91/03564  3/1991  WIPO .

OTHER PUBLICATIONS

A. Mustranta, P. Forssell, A–M. Aura, T. Suortti, and K. Poutanen, "Modification of Phospholipids with Lipases and Phospholipases", *Biocatalysis*, vol. 9, pp. 181–193 (1994).

*Primary Examiner*—Leslie Wong
*Attorney, Agent, or Firm*—Pennie & Edmonds LLP

[57] ABSTRACT

Improved process for the interesterification of a phospholipid with a triacyl glycerol is obtained by using an enzyme system containing immobilized lipase and immobilized phospholipase. The phospholipids obtained have better heat stabilized properties and better emulsifying properties than regular lecithin and may be used in emulsion systems or in coatings for instantized powders.

20 Claims, No Drawings

PROCESS FOR THE INTERESTERIFICATION OF PHOSPHOLIPIDS

TECHNICAL FIELD

The present invention relates to a process for exchanging acyl groups in a phospholipid by enzymatic ester exchange with a triacyl glycerol.

BACKGROUND ART

Glycerophospholipids such as phosphatidyl choline consist of glycerol esterified with two fatty acyl groups and one phosphate or esterified phosphate group. For some applications of the phospholipids it is desirable to exchange the acyl groups in the phospholipids, e. g. in order to improve their heat stability.

In this respect it was previously shown, e. g. in U.S. Pat. No. 5,314,706, that egg yolk fortified with exogenous lysophosphatidylcholine obtained by hydrolysis of lecithin with a phospholipase A2 improved the thermostability of emulsions, particularly mayonnaise.

Furthermore, it was shown in WO 91/03564 that enzymatic interesterification of a phospholipid with a fatty acid using a lipase catalyst immobilized on a macroporous carrier in an organic solvent gave rise to improved incorporation of specific acyl moieties in the phospholipid. In that process, a large excess of fatty acid was used which remains in the reaction mixture at the end of the process and which is not easily separated from the desired modified lecithin.

SUMMARY OF THE INVENTION

The present invention relates to a process to modify the fatty acid composition of the phospholipids to exchange the long-chain unsaturated fatty acids with short- and medium-chain fatty acids.

Very surprisingly, it has now been found possible to interestenrfy triglycerides with phospholipids in the presence of immobilized lipase and immobilized phospholipase and so to incorporate short-chain fatty acid moieties in the positions 1 and 2 of the glycerol moiety. No significant increase in free fatty acids was detected at any time during the reaction. Furthermore, it was surprising that the modified lecithin was a better emulsifier than natural lecithin for some emulsion systems such as e. g. mayonnaise and salad dressing. Also the wettability of powders, particularly lecithinized milk and cocoa powders, was dramatically improved when lecithin modified according to the process of the invention was used. Another decisive advantage of the modified lecithins obtained by the process of the invention is that they did not show any adverse flavors.

DETAILED DESCRIPTION OF THE PREFERRED EMBODIMENTS

The process according to the invention is characterized in that the reaction takes place in the absence of solvent with an enzymatic system consisting of a mixture of immobilized lipase and immobilized phospholipase.

The process of the invention may be applied to any desired kind of phospholipid containing fatty acid acyl ester groups. Examples of such naturally occuring phospholipids are phosphatidic acid, phosphatidyl choline, phosphatidyl serine, phosphatidyl glycerol, phosphatidyl inositol, phosphatidyl ethanolamine and diphosphatidyl glycerol. Synthetic phospholipids with various hydroxy compounds esterified to the phosphate group, 1-alkyl-2-acyl-phospholipids and diacyl-phospholipids may also be processed.

The exchange reaction may be used to incorporate any desired fatty acid moiety into a phospholipid. Of particular interest are short-chain e.g. C2–C4 saturated fatty acids and medium-chain e. g. C6–C12 saturated fatty acids moieties. All oils and fats containing a significant amount of these fatty acids moieties incorporated in triglycerides may be used as starting materials, especially short- to medium-chain triglycerides and butter oil, most preferably triacetin.

EXAMPLES

The enzyme catalyst to be used comprises a lipase which may be of animal, plant or microbial origin and may be positionally non specific or specific, e. g. Lypozyme(TM), Novo Nordisk a/s. It also comprises a phospholipase, preferably. an extracellular phospholipase A2, e. g. Lecitase (TM), Novo Nordisk a/s.

The enzymes used in the process of the invention are immobilized on a particulate macroporous organic or inorganic carrier, and are preferably attached to the carrier by cross-linking with any suitable cross-linking agent, e. g. glutaraldehyde.

The ratio of immobilized lipase to immobilized phospholipase is chosen so that the lipase represents 25 to 75% and preferably 30 to 70% by weight of the total beats of enzyme, which is also the same percentage of the total activity of the enzyme system.

The interesterifying process should be carried out under conditions in which optimal activity and thermostability of the immobilized enzymes are given, preferable at 60–80° C. and for 1 to 72 h, preferably for about 23 h. At the end of the reaction, the enzymes are separated, e. g. by filtering. One advantage of the present method is that, when it is necessary, the phospholipids can easily be separated from the triglycerides, particularly in the case where triacetin is used as the oil, since there is an immediate phase separation between the unreacted triacetin and the lecithin.

In case of any other triglyceride being used and a separation is desired, the classical lecithin purification methods, such as acetone fractionation or degumming, e. g. with about 0.3% phosphoric acid at about 90° C. can be applied. As an alternative, which is not preferred, the separation can take place by high performance thin layer chromatography (HPTLC).

The modified lecithins obtained by the process of the invention may be used in food emulsions, e. g. sauces, mayonnaise and salad dressings and are remarkable for their improved emulsifying properties as well as for the thermal stability of the products in which they are incorporated.

They may also be used in the manufacture of instantized powders, e. g. milk, cocoa, and coffee powders, where they provide better wettability than the regular lecithins.

The invention will be further illustrated by way of the following Examples in which parts and percentages are by weight unless otherwise specified.

In the Examples, the immobilized lipase used was Lipozyme (TM), Novo Nordisk a/s.

The immobilized phospholipase used was an extracellular phospholipase A2 immobilized on glass beads and prepared as follows: 0.5 g of glass beads (arnnopropylated, Sigma G-5019) were placed in 5 ml of degassed 100 micromolar $NaH_2PO_4$ buffer (pH 7) containing 2.5% glutaraldehyde and a vacuum was applied for 1 h. The beads were consecutively washed with water, a 0.5 molar solution of NaCl and a 100 millimolar solution of $NaH_2PO_4$ (pH 6). 1 ml Lecitase (TM), Novo Nordisk a/s and 4 ml of the latter degassed buffer were added to the beads and incubated at 4° C. overnight with slight agitation. After washing it again with the latter buffer, the beads were stored in a storage buffer.

Example 1

150 g of a mixture of demoistured lecithin:medium-chain triglycerides in the proportions 1:2 were mixed and heated up to 70° C. Then 1.5 g of immobilized Lipozyme (TM) and 0.3 g of the immobilized phospholipase A2 were added. The sample was incubated at this temperature for 23 h. The enzymes were retrieved by filtering. For the purpose of analysis, the fatty acid methyl esters (FAMES) were produced from the phospholipids by adding 400 microliter acetyl chloride (Fluka) and incubating for 20 min at 100° C. The phospholipids were separated from all the other components through HPTLC (plates of silicagel 60 F 254, Merk) in a two migration step, first with a mixture of toluene:hexane:formic acid in the proportions of 70:30:0.5 and then with a mixture of hexane:diethyl ether:formic acid in the proportions of 60:40:1, and extracted from the silicagel in 2 ml of a mixture of hexane:methanol in the proportions of 1:4. The FAMES obtained for the starting lecithin and for the lecithin modified according to the process of the invention were analyzed by gas chromatography. The figures given in following table 1 are based on the weight of the fatty acids.

TABLE 1

| Fatty acid | Starting lecithin | Modified lecithin |
|---|---|---|
| C 4:0 | — | — |
| C 6:0 | — | — |
| C 8:0 | — | 18.4 |
| C 10:0 | 0.1 | 9.1 |
| C 12:0 | — | — |
| C 14:0 | 1.8 | 1.5 |
| C 16:0 | 17.7 | 21.4 |
| C 18:0 | 5.9 | 4.1 |
| C 18:1 | 11.1 | 4.6 |
| C 18:2 | 57 | 35.7 |
| C 18:3 | 6.6 | 4.5 |

For the purpose of comparison, the same lecithin was treated either with immobilized Lecitase (TM) (comparison 1) or with immobilized Lipozyme (TM) (comparison 2). The amount of new fatty acids incorporated was 18 Mol % for comparison 1 and 27 Mol % for comparison 2, whereas it was 45% for the lecithin modified with the mixture of enzymes in the process of the invention.

Example 2

The process of Example 1 was used with the difference that the lecithin was reacted with triacetin. The ratio of demoisturized lecithin:triacetin was 1:1. The samples were left overnight to obtain an almost complete phase separation. The enzyme was retrieved by filtering. The upper phase, which represented the lecithin was analyzed for fatty acid composition, as described in Example 1, except that for better quantification of C 2:0, butylesters were made instead of methylesters, using a procedure well established in the literature. The figures given in following table 2 are based on the weight of the fatty acids.

TABLE 2

| Fatty acid | Modified lecithin |
|---|---|
| C 2:0 | 3.5 |
| C 4:0 | 0.3 |
| C 14:0 | 1.9 |
| C 16:0 | 24.5 |
| C 18:0 | 5.4 |
| C 18:1 | 11.3 |
| C 18:2 | 45.5 |
| C 18:3 | 7.7 |

Example 3

Salad dressings were prepared containing 30% soy bean oil, 60% water, 10% vinegar, 0.3% Xanthan gum and 1% lecithin modified as in Example 1. For the purpose of comparison, the same salad dressings were made with either regular lecithin (comparison 3) or a mixture of regular lecithin:medium chain triglyceride in the proportions of 2:1 (comparison 4), respectively.

Their heat stability was tested with respect to homogeneity and viscosity as follows:

20 ml of the respective salad dressing were incubated for 2 h at 80° C. (temperature of a water bath). After incubation, the sample with regular lecithin was non-homogeneous, some stratification was visible, whereas the sample with the modified lecithin was homogeneous without any stratification.

The viscosity was detected with a spoon test (drip a sample from the spoon) and with a Rheometer (shear rate versus shear stress). Both results indicated a higher viscosity of the samples with modified lecithin: at a shear rate of 240 /s, the shear stress was 160 for the sample with regular lecithin and about 185 for the sample with modified lecithin. Before the heat shock, both samples had a value of 185.

The medium chain triglycerides had no influence on any of these factors. The samples with the lecithin modified according to the invention were found to be more heat stable than the samples with the regular lecithin used (comparison 3) and with the mixture of regular lecithin and medium chain triglycerides. After centrifugation significantly less oil was found on the top, 0.25 g oil were recovered for a regular lecithin with (comparison 4) or without (comparison 3) medium chain triglyceride added compared to 0.18 g with the lecithin modified according to the invention. A marked reduction of off-flavors was also detected in the latter sample.

Example 4

The stabilizing effect of the modified lecithin according to the invention on egg yolk proteins was tested. 10 ml of 5–10 diluted homogenized egg yolk in vial, were heat shocked (h. s.) by placing the vial for 30 s in a 80° C. water bath.

The particle size (D(v, 0.9) in micrometer) was measured before and after heat shock. The results are given in following table 3.

TABLE 3

| D | No. Lec. | 0.5% Lec. | 0.5% Mod. Lec. | 1% Lec. | 1% Mod. Lec. | 2% Lec. | 2% Mod. Lec. |
|---|---|---|---|---|---|---|---|
| Before h.s. | 28 | 18 | 11 | 9 | 4 | 4 | 6 |

TABLE 3-continued

| D | No. Lec. | 0.5% Lec. | 0.5% Mod. Lec. | 1% Lec. | 1% Mod. Lec. | 2% Lec. | 2% Mod. Lec. |
|---|---|---|---|---|---|---|---|
| After h.s. | 75 | 60 | 41 | 55 | 17 | 15 | 13 |

It could be observed that the samples with the lecithin modified according to the invention were more stable. In general it can be stated that the same stabilizing effect of the lecithin can be achieved with half of the amount of lecithin modified according to the invention.

Example 5

Entire mayonnaise made of 50 g egg yolk, 3 g salt, 5 g mustard, 200 g vegetable oil, 3 g vinegar, 5 ml lemon juice and 6 ml water was produced without lecithin or with different levels of regular or modified lecithin added. 100 g of each mayonnaise were placed into jars, sealed and incubated for 2×30 min at 100° C. Then the oil on the top was completely decanted and measured. The results are given in following table 4.

TABLE 4

| Sample | Amount of oil on top after heat treatment, g |
|---|---|
| No lecithin added | 13.2 |
| 1% regular lecithin added | 6 |
| 1.5% regular lecithin added | 5 |
| 1% lecithin modified as in Example 1 added | 3.5 |
| 2% lecithin modified as in Example 1 added | 1.1 |
| 1% lecithin modified as in Example 2 added | 1 |
| 2% lecithin modified as in Example 2 added | 0.5 |
| 1% lysolecithin added | 2.2 |
| 2% lysolecithin (Emulfluid (TM), Lukas Meyer) added | 1 |

Again, it was observed that about half the amount or less of the lecithin modified according to the invention had the same stabilizing effect as a comparable amount of regular lecithin and had even a better stabilizing effect than a commercial lysolecithin.

Example 6

The regular or modified lecithin (as in Example 2) was dissolved in hexane respectively and then sprayed onto milk powder while mixing. The hexane was then evaporated while stirring.

For measuring the wettability, 5 g of milk powder were spooned onto 100 ml water at room temperature and the time was measured until the milk powder sank under the surface completely. The times indicate that regular lecithin improves the wettability of milk powder dramatically, but it was also seen that the lecithin modified according to Example 2 performs even better.

The results of the drowning times are given in following table 5.

TABLE 5

| Sample | Drowning time, s |
|---|---|
| Pure milk powder | >120 |
| Milk powder + 0.5% lecithin | 21 |
| Milk powder + 0.5% modified lecithin | 9 |
| Milk powder + 1% lecithin | 15 |
| Milk powder + 1% modified lecithin | 7 |

Example 7

In the same respect as in Example 6, an instant cocoa preparation containing sucrose, dutched cocoa powder, cocoa flavour and 1% lecithin was tested. Two samples were prepared containing 1% of regular lecithin or with triacetin modified lecithin (as in Example 2), respectively.

The samples were steam agglomerated and produced as commercial cocoa preparation. For evaluation of wettability, 21 g of the milk preparation were added on 250 ml milk at room temperature and the time was measured until all material was drowned. The samples were observed over several days. The results are given in following table 6.

TABLE 6

| Drowning time in s. (days) | Regular lecithin | Modified lecithin |
|---|---|---|
| 0 | 15 | 11 |
| 3 | 35 | 17 |
| 5 | 32 | 13 |
| 7 | 35 | 10 |
| 10 | 40 | 15 |
| 21 | 35 | 12 |
| 28 | 37 | 16 |
| 35 | 42 | 19 |
| 42 | 39 | 17 |

Example 8

ODELL'S (TM) clarified butter, having a moisture content of at most 0.1% was mixed with lecithin in a ratio of 2:1 and immobilized lipases and phospholipases were added as in the previous Examples. The reaction conditions were also as described before. The modified lecithin obtained had a fatty acid composition as shown in the following table 7.

TABLE 7

| Fatty acid | Modified lecithin |
|---|---|
| C 4:0 | 1.2 |
| C 6:0 | 0.8 |
| C 8:0 | 1.5 |
| C 10:0 | 1.4 |
| C 12:0 | 3 |
| C 14:0 | 11.9 |
| C 16:0 | 20.9 |
| C 18:0 | 22.4 |
| C 18:1 | 17.9 |
| C 18:2 | 15.3 |
| C 18:3 | 3 |

What is claimed is:
1. A process for modifying a phospholipid material which comprises exchanging acyl groups in a phospholipid by enzymatic exchange with a triacyl glycerol that contains $C_2$–$C_{12}$ saturated acyl groups, the reaction being conducted in the absence of a solvent with an enzymatic system consisting essentially of a mixture of an immobilized lipase and an immobilized phospholipase and at a sufficient temperature and for a sufficient time to exchange acyl groups in the phospholipid material and form a modified phospholipid material.

2. A process as claimed in claim 1, wherein the lipase represents 25 to 75% of the total activity of the enzymatic system.

3. A process as claimed in claim 2, wherein the lipase represents 30 to 70% of the total activity of the enzymatic system.

4. A process as claimed in claim 1, wherein the triacyl glycerol essentially contains medium-chain C6–C12 saturated acyl groups.

5. A process as claimed in claim 1, wherein the phospholipid is a naturally occuring lecithin.

6. The process of claim 1 wherein the lipase and phospholipase each is immobilized on a particulate macroporous carrier and represents 25 to 75% of the total activity of the enzymatic system.

7. The process of claim 1 wherein the reaction is conducted at a temperature of 60 to 80° C. for a time of between 1 and 72 hours.

8. A process for modifying a phospholipid material which comprises exchanging acyl groups in a phospholipid by enzymatic exchange with a triacyl glycerol that contains $C_2$–$C_4$ saturated acyl groups, the reaction being conducted in the absence of a solvent with an enzymatic system consisting essentially of a mixture of an immobilized lipase and an immobilized phospholipase and at a sufficient temperature and for a sufficient time to exchange acyl groups in the phospholipid material and form a modified phospholipid material.

9. A process as claimed in claim 8, wherein the lipase represents 25 to 75% of the total activity of the enzymatic system.

10. A process as claimed in claim 8, wherein the lipase represents 30 to 70% of the total activity of the enzymatic system.

11. A process as claimed in claim 8, wherein the phospholipid is a naturally occurring lecithin.

12. The process as claimed in claim 8 wherein the lipase and phospholipase each is immobilized on a particulate macroporous carrier and represents 25 to 75% of the total activity of the enzymatic system.

13. The process as claimed in claim 8 wherein the reaction is conducted at a temperature of 60 to 80° C. for a time of between 1 and 72 hours.

14. The process as claimed in claim 8 where in said triacyl glycerol is triacetin.

15. A food product which includes therein a modified phospholipid according to claim 8.

16. The food product of claim 15 in the form of an emulsion.

17. The food product according to claim 16 in the form of a sauce, a mayonnaise or a salad dressing.

18. The food product according to claim 16 wherein the modified phospholipid is present in an amount of between 1 and 2 wt. %.

19. The food product according to claim 15 in the form of an instantized powder which includes as a coating thereon the modified phospholipid.

20. The food product according to claim 19 wherein the modified phospholipid is present in the coating in an amount of between about 0.5 and 1 wt. %.

* * * * *